United States Patent
Shin et al.

(10) Patent No.: US 8,420,878 B2
(45) Date of Patent: Apr. 16, 2013

(54) COMPLEX OXIDE CATALYST OF BI/MO/FE FOR THE OXIDATIVE DEHYDROGENATION OF 1-BUTENE TO 1,3-BUTADIENE AND PROCESS THEREOF

(75) Inventors: Chae-Ho Shin, Daejeon (KR); Jung-Hyun Park, Chungbuk (KR); Eunae Noh, Chungbuk (KR); Kyoungho Row, Daejeon (KR); Ji Won Park, Gwangju (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 599 days.

(21) Appl. No.: 12/577,869

(22) Filed: Oct. 13, 2009

(65) Prior Publication Data
US 2010/0099936 A1 Apr. 22, 2010

(30) Foreign Application Priority Data
Oct. 17, 2008 (KR) .................. 10-2008-0102154

(51) Int. Cl.
C07C 5/333 (2006.01)
B01J 23/18 (2006.01)

(52) U.S. Cl.
USPC .......... 585/631; 502/311; 502/313; 502/314; 502/316; 502/321

(58) Field of Classification Search .......... 502/311, 502/313, 314, 316, 321; 585/631
See application file for complete search history.

(56) References Cited

U.S. PATENT DOCUMENTS

| | | | |
|---|---|---|---|
| 3,110,746 A | 11/1963 | Voge et al. | |
| 3,806,470 A | 4/1974 | Aykan et al. | |
| 3,843,553 A | 10/1974 | Aykan et al. | |
| 3,843,554 A | 10/1974 | Aykan et al. | |
| 3,937,748 A | 2/1976 | Miklas | |
| 4,018,712 A * | 4/1977 | Li | 502/249 |
| 4,040,978 A * | 8/1977 | Li | 502/212 |
| 4,062,885 A * | 12/1977 | Mekhtiev et al. | 558/327 |
| 4,162,234 A * | 7/1979 | Grasselli et al. | 502/205 |
| 4,192,776 A * | 3/1980 | Grasselli et al. | 502/205 |
| 4,250,346 A * | 2/1981 | Young et al. | 585/658 |
| 4,309,361 A * | 1/1982 | Suresh et al. | 558/324 |
| 4,438,217 A * | 3/1984 | Takata et al. | 502/205 |
| 4,442,308 A * | 4/1984 | Arntz et al. | 568/480 |

(Continued)

FOREIGN PATENT DOCUMENTS

| | | |
|---|---|---|
| GB | 1 366 375 | 9/1974 |
| KR | 57-17575 B | 4/1982 |
| KR | 10-2007-0103219 A | 10/2007 |
| KR | 100847206 B | 7/2008 |

OTHER PUBLICATIONS

Voge, Hervey H. et al.: "Catalytic Oxidation of Olefins", *Adv. Catal. Related Sub.*, 17, 1967, pp. 151-153.

(Continued)

*Primary Examiner* — Cam N. Nguyen
(74) *Attorney, Agent, or Firm* — Frommer Lawrence & Haug LLP; Ronald R Santucci

(57) ABSTRACT

The present invention relates to a complex oxide catalyst of Bi/Mo/Fe and an oxidative dehydrogenation of 1-butene in the presence of a catalyst herein. A catalyst of the present invention is superior to the conventional Bi/Mo catalyst in thermal and mechanical stabilities, conversion and selectivity toward 1,3-butadiene, while showing a long-term catalytic activity.

4 Claims, 3 Drawing Sheets

U.S. PATENT DOCUMENTS

| | | | | |
|---|---|---|---|---|
| 4,590,011 | A | * | 5/1986 | Li .................................. 558/323 |
| 4,600,541 | A | * | 7/1986 | Aoki et al. .................... 558/321 |
| RE32,484 | E | * | 8/1987 | Grasselli et al. .............. 502/212 |
| 4,916,103 | A | * | 4/1990 | Martan et al. ................. 502/212 |
| 5,072,052 | A | * | 12/1991 | Boeck et al. .................. 568/479 |
| 5,144,090 | A | * | 9/1992 | Honda et al. .................. 568/476 |
| 5,250,485 | A | * | 10/1993 | Kuroda et al. ................. 502/159 |
| 5,300,707 | A | * | 4/1994 | Caillod et al. ................ 568/480 |
| 5,532,199 | A | * | 7/1996 | Watanabe et al. ............. 502/311 |
| 5,856,259 | A | * | 1/1999 | Watanabe et al. ............. 502/305 |
| 6,080,893 | A | * | 6/2000 | Hecquet et al. ............... 568/479 |
| 6,383,973 | B1 | * | 5/2002 | Kimura et al. ................. 502/300 |
| 6,383,976 | B1 | * | 5/2002 | Arnold et al. ................. 502/311 |
| 6,441,227 | B1 | * | 8/2002 | Karim et al. .................. 562/548 |
| 6,479,691 | B1 | * | 11/2002 | Sasaki et al. ................. 558/321 |
| 6,610,629 | B2 | * | 8/2003 | Hinago et al. ................ 502/300 |
| 6,620,973 | B2 | * | 9/2003 | Karim et al. .................. 568/478 |
| 6,645,906 | B2 | * | 11/2003 | Bogan et al. .................. 502/311 |
| 6,740,769 | B1 | * | 5/2004 | Mizutani et al. .............. 558/324 |
| 7,387,982 | B2 | * | 6/2008 | Kondo et al. .................. 502/311 |

OTHER PUBLICATIONS

Soares, Ana Paula Vieira et al.: "Synergy effects between β and γ phases of bismuth molybdates in the selective catalytic oxidation of 1-butene", *Applied Catalysis A: General*, 253, 2003, pp. 191-200.

Misono, Makoto et al.: "Catalytic Properties of Iron Oxide. III. Oxidative Dehydrogenation of Butenes over Iron Oxide Catalysts", *Bull. Chem. Soc. Jpn.*, vol. 53, No. 3, 1980, pp. 648-652.

Kung, H.H. et al.: "Selectivity in the Oxidative Dehydrogenation of Butene on Zinc-Iron Oxide Catalyst", *J. Phys. Chem.*, 84, 1980, pp. 382-388.

Botavina, M.A. et al.: "Oxidative dehydrogenation of $C_3$-$C_4$ paraffins in the presence of $CO_2$ over $CrO_x/SiO_2$ catalysts"; *Applied Catalysis A: General*, 347, 2008, pp. 126-132.

Niwa, Miki et al.: "Study on Olefin Oxidation by Periodic-Pulse Technique, II. Oxidative Dehydrogenation of 1-Butene Using Various Oxide Catalysts", *Journal of Catalysis*, 27, 1972, pp. 26-33.

Toledo-Antonio, J.A. et al.: "Correlation between the magnetism of non-stoichiometric zinc ferrites and their catalytic activity for oxidative dehydrogenation of 1-butene", *Applied Catalysis A: General*, 234, 2002, pp. 137-144.

Krishnan, Venkatesan V. et al.: "Oxidative Dehydrogenation of 1-Butene over Manganese Oxide Octahedral Molecular Sieves", *Journal of Catalysis*, 184, 1999, pp. 305-315.

Yang, B.L. et al.: "Crystallite size effect in the selective oxidation of butane to butadiene on iron oxide. 2. Reaction Studies", *The Journal of Physical Chemistry*, 88 (12), 1984, pp. 2531-2534.

Linn, W.J. et al.: "Oxidation of 1-Butene over Bismuth Molybdates and Bismuth Iron Molybdate", *Journal of Catalysis*, 41, 1976, pp. 134-139.

\* cited by examiner ent of Korean Patent Application No. 10-2008-0102154 filed Oct. 17, 2008, the entire contents of which are incorporated herein by reference.

COMPLEX OXIDE CATALYST OF BI/MO/FE FOR THE OXIDATIVE DEHYDROGENATION OF 1-BUTENE TO 1,3-BUTADIENE AND PROCESS THEREOF

CROSS-REFERENCE TO RELATED APPLICATION

This application claims under 35 U.S.C. §119(a) the benefit of Korean Patent Application No. 10-2008-0102154 filed Oct. 17, 2008, the entire contents of which are incorporated herein by reference.

BACKGROUND (a) Technical Field

The present invention relates to a catalyst that can be used in a process of preparing 1,3-butadiene, and particularly to a multi-component Bi/Mo/Fe-based oxide catalyst, which is prepared by co-precipitation in a pH-adjusted solution and shows superior selectivity towards 1,3-butadiene using n-butene (1-, 2-, iso-butene), while exhibiting a relatively slow deactivation. The present invention also relates to a process of preparing the catalyst. A process of 1,3-butadiene using the catalyst is also disclosed in the present invention.

(b) Background Art

Lower olefins such as ethylene, propylene, butene and butadiene have been used as raw materials of polyolefins and the starting materials for various chemicals in the petrochemical industry. Although the thermal cracking of naphtha is still a major process for the production of lower olefins, various processes such as the thermal cracking of ethane and fluid catalyst cracking produce the lower olefins as supplementary process. However, the thermal cracking has become important as supplementary production process of the lower olefins. The high temperature operation of the thermal cracking process inevitably requires a large amount of energy. However, it is widely used because of the simplicity and convenience in process operation. However, the construction of new naphtha cracker becomes difficult because naphtha cracking produces side products other than butadiene and production cost increases considerably due to the increase in the cost of naphtha and energy.

Another method of preparing butadiene is a direct hydrogenation of n-butene. This is an endothermal reaction requiring much energy, and forms coke on the surface of a catalyst thus decreasing the activity of the catalyst. Various attempts have been made to overcome these drawbacks.

It is possible to obtain butadiene by oxidative dehydrogenation (ODH) of n-butene. ODH is an exothermal reaction and can be conducted at a relatively low temperature, thereby reducing the amount of energy consumption. This is also advantageous in that it can prevent the production of coke and also the presence of oxygen results in significant decrease of cracking and formation of coke. Examples of the conventional oxidants include oxygen, sulfur compounds, carbon dioxide and steam [M. A. Botavina, G. Martra, Yu. A. Agafonov, N. A. Gaidai, N. V. Nekrasov, D. V. Trushin, S. Coluccia and A. L. Lapidus, *Appl. Catal. A: Gen.*, 347, 126 (2008)].

Various metal oxides are used as catalysts in the ODH of butene [E. J. Miklas, U.S. Pat. No. 3,937,748 (1976), H. H. Kung, B. Kundalkar, M. C. Kung and W. H. Cheng, *J. Phys. Chem.*, 84, 382 (1980), M. Misono, K. Sakata, F. Ueda, Y. Nozawa and Y. Yoneda, *Bull. Chem. Soc. Jpn.*, 53, 648 (1980), B. L. Yang, F. Hong and H. H. Kung, *J. Phys. Chem.*, 88, 2531 (1984), V. V. Krishnan and S. L. Suib, *J. Catal.*, 184, 305 (1999), J. A. Toledo-Antonio, N. Nava, M. Martinez and X. Bokhimi, *Appl. Catal. A: Gen.*, 234, 137 (2002). In particular, Bi Mo complex oxide catalyst, a complex of Bi oxide and Mo oxide, has been reported as having superior catalytic activity [M. Niwa and Y. Murakami, *J. Catal.*, 27, 26 (1972); W. J. Linn and A. W. Sleight, *J. Catal.*, 41, 134 (1976); A. P. V. Soares, L. D. Dimitrov, M. C.-R. Andre de Oliveria, L. Hilaire, M. F. Portela and R. K. Grasselli, *Appl. Catal. A: Gen.*, 253, 191 (2003)].

In the ODH of n-butene, n-butene binds to $Mo^{6+}$ ions, and electrons produced in the binding reduce other $Mo^{6+}$ ions to provide $Mo^{5+}$ ions. The produced $Mo^{5+}$ ions react with $Bi^{3+}$ ions and $Mo^{6+}$ ions are regenerated. The reduced $Bi^{2+}$ ions are oxidized again after the reaction with oxygen. Contents of Bi and Mo are very important because Bi Mo catalyst experiences such an oxidation-reduction mechanism.

According to the molar ratio of Bi and Mo and the catalyst manufacture conditions, Bi Mo oxide catalysts are classified into α-phase ($Bi_2O_3 3MoO_3$), β-phase ($Bi_2O_3 2MoO_3$) and γ-phase ($Bi_2O_3 MoO_3$). The β-phase and the γ-phase Bi molybdate catalyst have been reported as having superior catalytic activity [H. H. Voge and C. R. Adams, *Adv. Catal. Related Sub.*, 17, 151 (1967)]. Korean patent No. 10-0847206 discloses that iron ferrite is a superior catalyst for the preparation of 1,3-butadiene. Korean patent publication No. 10-2007-0103219 discloses a Bi molybdate catalyst, its preparation method and a process of preparing 1,3-butadiene by using the catalyst.

The ODH of butene is conducted at the temperature of 400° C. or higher. Moreover, water is supplied as a reactant and also produced during the reaction. This requires the hydrothermal stability of catalyst and the mechanical stability against the valence change of metal. On the other hand, if the number of active site on catalyst surface is too large, allyl intermediate is polymerized and coke production causes a relatively fast deactivation. When the number of active site is too small, conversion and yield of 1,3-butadiene (1,3-BD yield) can be lowered. Consequently, the active material which increases the mechanical strength and catalytic activity is necessary. Catalytic activity can be maintained and 1,3-BD yield can be improved when electron migration between complex oxides is facilitated and oxidation-reduction is thus promoted.

Bi Mo oxide was considered as a preferable catalyst in the conventional process of preparing 1,3-butadiene. However, despite its relatively high reaction activity and 1,3-BD yield, the Bi Mo (BM) catalyst changes into various phases and significantly varies in activity depending on the synthesis conditions and Bi Mo contents. In particular, although β-Bi Mo having a Bi/Mo molar ratio of 1 shows the highest activity, it disadvantageously changes into various phases at a particular temperature or higher. It also causes mechanical fatigue depending on the change in the valence during the reaction, thus lowering catalytic properties.

SUMMARY OF THE DISCLOSURE

The present inventors propose a complex metal oxide catalyst prepared by adding Fe to an oxide catalyst comprising only Bi and Mo to increase mechanical and hydrothermal stability and homogeneity.

A BM catalyst used as a catalyst in the process of preparing 1,3-butadiene has high reaction activity and 1,3-BD yield. However, this catalyst changes into various phases during the reaction and undergoes drastic changes in its catalytic activity depending on the synthesis conditions and Bi and Mo contents. In particular, despite its highest activity, β-Bi Mo, where Bi/Mo molar ratio is 1, is disadvantageous in that it changes into various phases at a certain temperature or above. Moreover, the valence changes during the reaction and causes mechanical fatigue, thereby decreasing catalytic properties.

The present invention provides a complex metal oxide catalyst that further comprises Fe to increase mechanical and hydrothermal stability and homogeneity. This complex metal oxide catalyst shows mechanical stability due to the addition of Fe, and the stability under a reductive condition is improved, thus inhibiting structural change caused by repeated phase transition. The catalyst herein exhibits a relatively slow deactivation, while 1,3-BD yield is increased during the oxidative dehydrogenation of 1-butene.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

Figure 1:
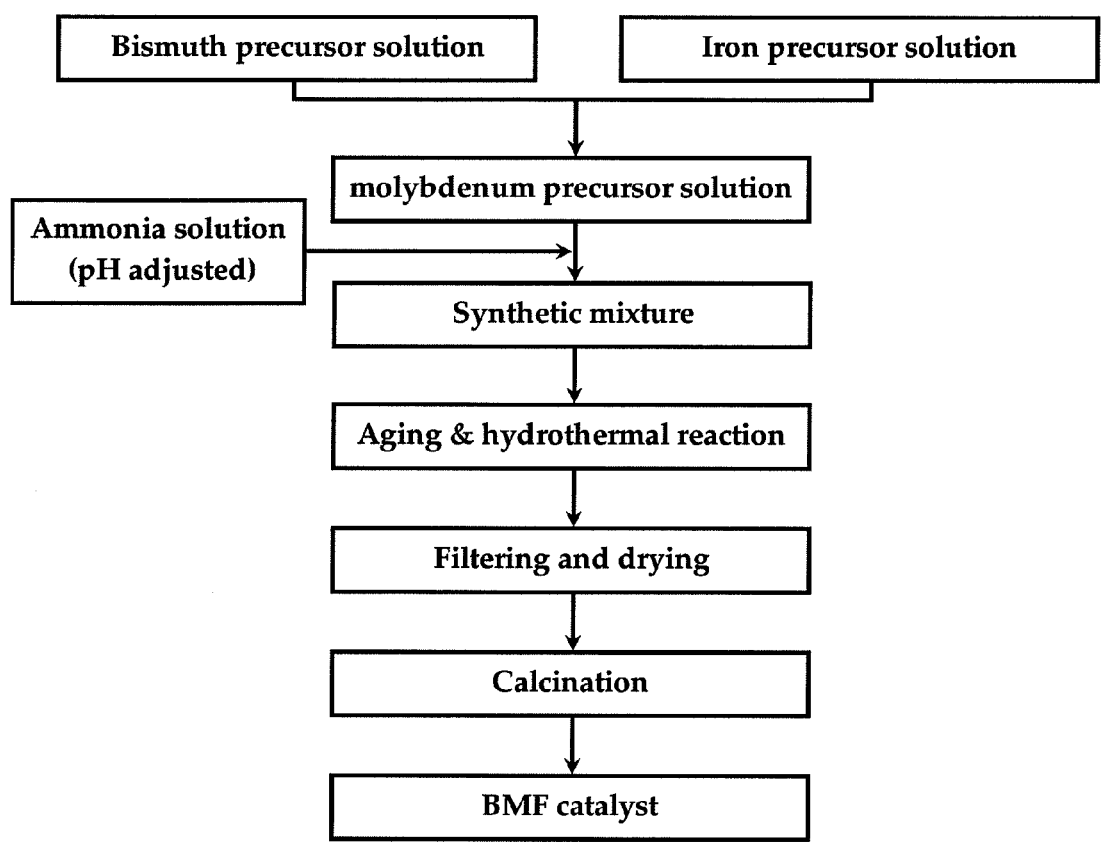
FIG. 1 is a flow chart of the preparation of complex oxide catalyst of Bi/Mo/Fe (BMF)

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Reference will now be made in detail to the preferred embodiments of the present invention, examples of which are illustrated in the drawings attached hereinafter, wherein like reference numerals refer to like elements throughout. The embodiments are described below so as to explain the present invention by referring to the figures.

In an aspect, the present invention discloses a BMF catalyst for the preparation of 1,3-butadiene, the catalyst comprising Bi, Mo and Fe in a molar ratio of 1:0.6-1:0.1-1.25.

In another aspect, the present invention discloses a process of preparing BMF catalyst for the preparation of 1,3-butadiene, which comprises (a) mixing a Bi precursor solution and a Fe precursor solution; (b) adding the mixed solution to a Mo precursor solution and adjusting the pH with a basic solution; (c) conducting a hydrothermal reaction of the pH-adjusted solution to provide a product of the hydrothermal reaction; and (d) drying and calcination the product.

In an embodiment, the present invention discloses a process of preparing BMF catalyst for the preparation of 1,3-butadiene, where the Bi precursor solution is a mixed solution comprising bismuth nitrate ($Bi(NO_3)_3.5H_2O$) and nitric acid ($HNO_3$) or a mixed solution of bismuth acetate ($Bi(CH_3CO_2)_3$) and acetic acid ($CH_3COOH$).

In another embodiment, the present invention discloses a process of preparing BMF catalyst for the preparation of 1,3-butadiene, where the Fe precursor solution is a mixed solution comprising iron nitrate ($Fe(NO_3)_3.9H_2O$) and nitric acid or a mixed solution of iron chloride ($FeCl_2.4H_2O$) and hydrochloric acid (HCl).

In still another embodiment, the present invention discloses a process of preparing BMF catalyst for the preparation of 1,3-butadiene, where the Mo precursor solution is a mixed solution comprising ammonium molybdate (($NH_4)_6Mo_7O_{24}.4H_2O$).

In yet another embodiment, the present invention discloses a process of preparing BMF catalyst for the preparation of 1,3-butadiene, where the basic solution is ammonia water, sodium carbonate ($Na_2CO_3$) and potassium carbonate ($K_2CO_3$) solution.

In still yet another embodiment, the present invention discloses a process of preparing BMF catalyst for the preparation of 1,3-butadiene, where the pH value is adjusted in the range of 3-9.

In a further embodiment, the present invention discloses a process of preparing BMF catalyst for the preparation of 1,3-butadiene, where the BMF catalyst is calcined at 450-750° C.

In still another aspect, the present invention discloses a process of preparing 1,3-butadiene, which comprising conducting an ODH of 1-butene in the presence of a catalyst herein.

In an embodiment, the present invention discloses a process of preparing 1,3-butadiene, where the oxidative dehydrogenation is conducted at 350-450° C. and a WHSV of 1.0-5.0.

The present invention discloses a catalyst exhibits a relatively higher selectivity toward 1,3-butadiene, while showing a relatively slower deactivation, in an oxidative dehydrogenation of preparing 1,3-butadiene from 1-butene. The present invention also discloses a process of preparing such catalyst. A complex metal oxide catalyst used in an oxidative dehydrogenation of 1-butene varies in catalytic activity and reaction yields depending on the kind of precursors and process conditions. Therefore, a complex metal oxide having superior crystalline structure and 1,3-BD yields can be prepared by mixing precursor solutions and conducting co-precipitation under particular conditions. FIG. 1 shows the process of preparing such complex metal oxides.

The addition of Fe oxide to a BM catalyst increases catalytic activity and improves the stability under reductive conditions. Due to stability even under reductive conditions, active sites reduced by olefin during a partial oxidation can be easily oxidized and restored to the original state. Iron (Fe) increases the catalytic stability and activity by promoting the oxidation of active sites. Besides the Bi—Mo—O structure, new type of active sites such as Fe-added $Bi_3Mo_2FeO_{12}$ and $Fe_2(MoO_4)_3$ are produced, thereby increasing catalytic activity.

The BMF catalyst contains various phase depending on the Fe content, thus resulting in a remarkable change in activity or yield of 1,3-butadiene conversion. In the present invention, Bi/Mo molar ratio is preferred to be in the range of 1-1.5, preferably 1.0 to prepare a complex oxide catalyst. Fe/Bi molar ratio is preferred to be adjusted in the range of 0.01-2, preferably 0.1-1.25. The pH value of the mixture solution was controlled to 3-9 (preferably 5-7), using ammonia solution. When the pH value is outside the range, only a small amount of catalyst may be co-precipitated, and the obtained catalyst may exist in various phases, thus significantly decreasing reaction activity.

Solid product are obtained by stirring the mixed solution, while evaporating upper layer of the solution with an evaporator, and thus obtained product is dried at 25-140° C., preferably 110° C., for 24 hours. The product is sintered in an electric furnace under an air current at 450-750° C., preferably 450-550° C., for 2 hours to provide catalyst. When the calcination temperature is too low, ammonia ($NH_4^+$) or nitric acid ion (nitrate, $NO_3^-$) can remain after the synthesis and serve as a catalytic poison. When the calcination temperature is too high, the state of metal oxide can be changed and aggregation can occur, thus decreasing active sites of catalyst.

using an evaporator while hydrothermal reaction was conducted at 60° C., and dried with a drier at 110° C. for 24 hours. The products were sintered in an electric furnace at 550° C. to give a BMF catalyst.

Yields are shown in Table 1. The molar ratio of Bi and Mo was controlled to 1:1 in complex metal oxide catalyst, and the catalyst was denoted by using the relative molar amount of Fe. Table 1 shows catalysts with various ingredient ratios. BMF 1.0 refers to a complex metal oxide catalyst comprising Bi and Mo in a molar ratio of 1:1 along with one mole of Fe.

Yield, surface area, pore volume and X-ray diffraction pattern were analyzed, and the results are provided in Table 1.

TABLE 1

Yield and physicochemical properties of BMF catalyst

| Catalyst | Component (molar ratio) Bi | Mo | Fe | Yield (%) | X-ray diffraction analysis | Surface area ($m^2/g$) | Pore volume ($cm^3/g$) |
|---|---|---|---|---|---|---|---|
| BMF 0.10 | 1 | 1 | 0.10 | 88 | $Bi_2O_32MoO_3, Bi_2O_3MoO_3 >$ $Bi_3Mo_2FeO_{12} > Bi_2O_33MoO_3$ | 1.4 | 0.01 |
| BMF 0.20 | 1 | 1 | 0.20 | 96 | $Bi_2O_32MoO_3, Bi_2O_3MoO_3 >$ $Bi_3Mo_2FeO_{12} > Bi_2O_33MoO_3$ | 2.6 | 0.01 |
| BMF 0.35 | 1 | 1 | 0.35 | 99 | $Bi_2O_32MoO_3, Bi_2O_3MoO_3 >$ $Bi_3Mo_2FeO_{12} > Bi_2O_33MoO_3$ | 2.8 | 0.01 |
| BMF 0.50 | 1 | 1 | 0.50 | 88 | $Bi_3Mo_2FeO_{12} > Fe_2(MoO_4)_3$ | 3.1 | 0.01 |
| BMF 0.65 | 1 | 1 | 0.65 | 93 | $Bi_3Mo_2FeO_{12} > Fe_2(MoO_4)_3$ | 3.6 | 0.02 |
| BMF 0.75 | 1 | 1 | 0.75 | 91 | $Bi_3Mo_2FeO_{12} > Fe_2(MoO_4)_3$ | 3.8 | 0.02 |
| BMF 0.85 | 1 | 1 | 0.85 | 91 | $Bi_3Mo_2FeO_{12} > Fe_2(MoO_4)_3$ | 3.5 | 0.03 |
| BMF 1.00 | 1 | 1 | 1.00 | 79 | $Bi_3Mo_2FeO_{12} > Fe_2(MoO_4)_3$ | 3.4 | 0.04 |
| BMF 1.25 | 1 | 1 | 1.25 | 92 | $Bi_3Mo_2FeO_{12} > Fe_2(MoO_4)_3$ | 4.1 | 0.04 |

The ODH over the complex metal oxide catalyst is carried out in an atmospheric fixed-bed reactor system at 350-500° C., preferably 380-430° C. The molar ratio of 1-butene:air: steam is preferred to be controlled in the range of 1.0:2-6:1-10, preferably 1.0:2-4:5.0-8.0. WHSV (weight hourly space velocity) is maintained to 2.4 $h^{-1}$ based on 1-butene. After water is removed, products are passed through a cooler and analyzed by using a gas chromatography equipped with a thermal conductivity detector and a flame ionization detector.

EXAMPLES

The following examples illustrate the invention and are not intended to limit the same.

Example 1

Preparation of BMF Catalyst Comprising Bi and Mo in a Molar Ratio of 1:1 with Various Content of Fe BMF catalyst for preparing 1,3-butadiene from 1-butene was prepared using a hydrothermal reaction by co-precipitation.

16.5 g of bismuth nitrate ($Bi(NO_3)_3 \cdot 5H_2O$, Aldrich, 98%) and 8.5 g of nitric acid ($HNO_3$, SAMCHUN, 60%) were dissolved in 60 g of distilled water, and sufficiently stirred at 60° C. 8.9 g of iron nitrate ($Fe(NO_3)_3 \cdot 9H_2O$, Junsei, 98%) and 5.5 g of nitric acid were dissolved in 60 g of distilled water g, and sufficiently stirred at 60° C. These two solutions were slowly added while stirring in a mixture of 5.9 g of ammonium molybdate (($NH_4)_6Mo_7O_{24}4H_2O$, Wako Pure Chemical, 81%) and 60 g of distilled water.

Figure 2:
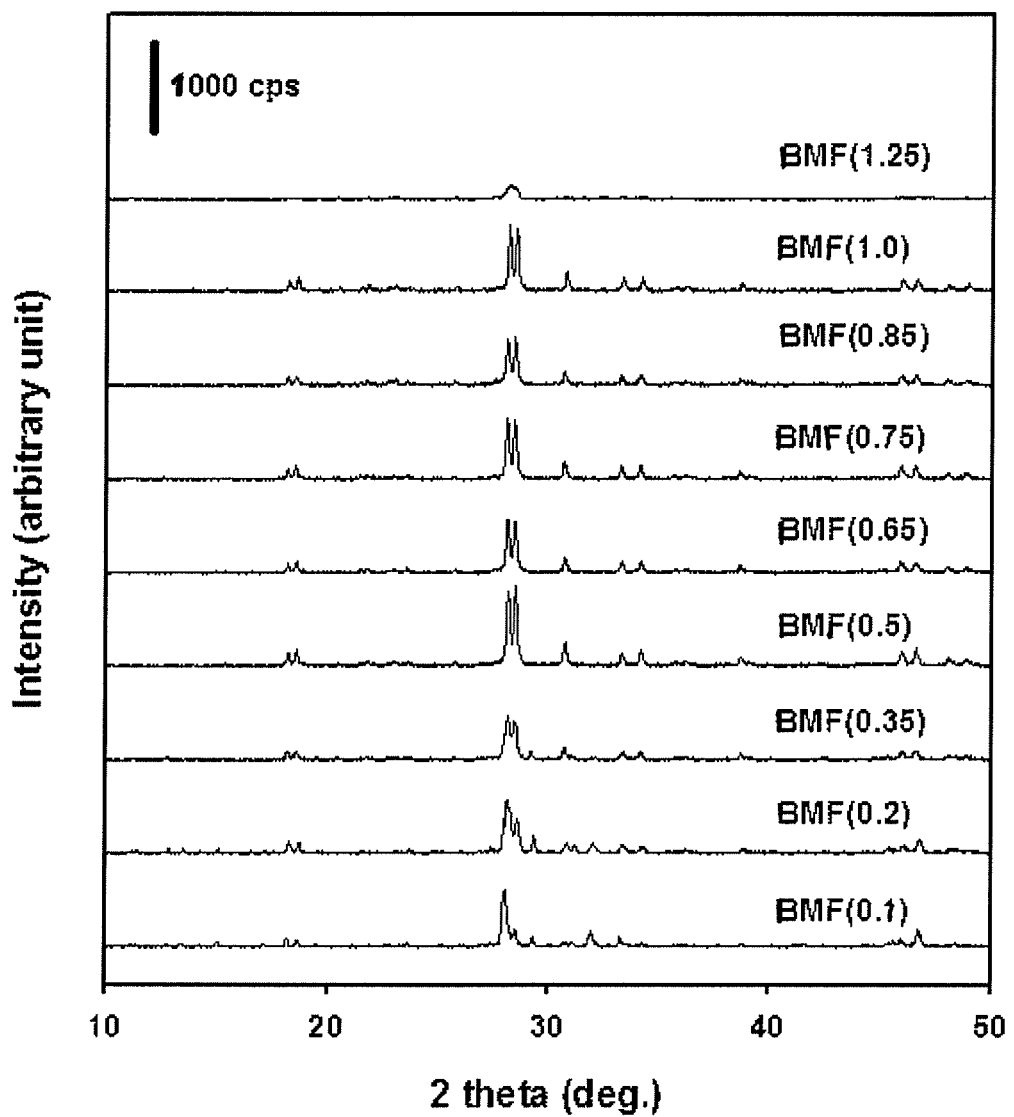
FIG. 2 shows X-ray diffraction pattern of complex oxide catalyst of Bi/Mo/Fe prepared in example 1.

Ammonia water ($NH_4OH$, Daekwang Chemistry, 28%) was slowly added, while adjusting the pH of the mixed solution to 5.0. Co-precipitated solid products were obtained by According to X-ray diffraction pattern of a complex metal oxide catalyst, the diffraction peaks of β- and γ-phase (Bi Mo phase) were observed at the Fe content of 0.35 moles or less (FIG. 2). As the Fe content increases, the diffraction peaks of and γ-phase disappear and the diffraction peaks of a complex metal oxide ($Bi_3FeMo_2O_{12}$) increases. This ascertains that the added Fe is bound with Bi or Mo and exists in the form of a complex metal oxide. A trace amount of $Fe_2(MoO_4)_3$ coexists besides $Bi_3FeMo_2O_{12}$ phase.

Example 2

Preparation of BMF Catalyst Comprising Bi and Mo in a Molar Ratio of 1:1 at Various Calcination Temperature To study the influence of calcination temperature, the BMF 0.75 catalyst prepared in Example 1 was dried at 110° C. for 24 hours, and sintered in an electric furnace at 450, 550, 650 or 750° C. to provide complex metal oxide catalysts.

Thus obtained complex metal oxide catalyst was denoted as BMF 0.75 with the calcination temperature. BMF 0.75-550 refers to a complex metal oxide catalyst sintered at 550° C.

Figure 3:
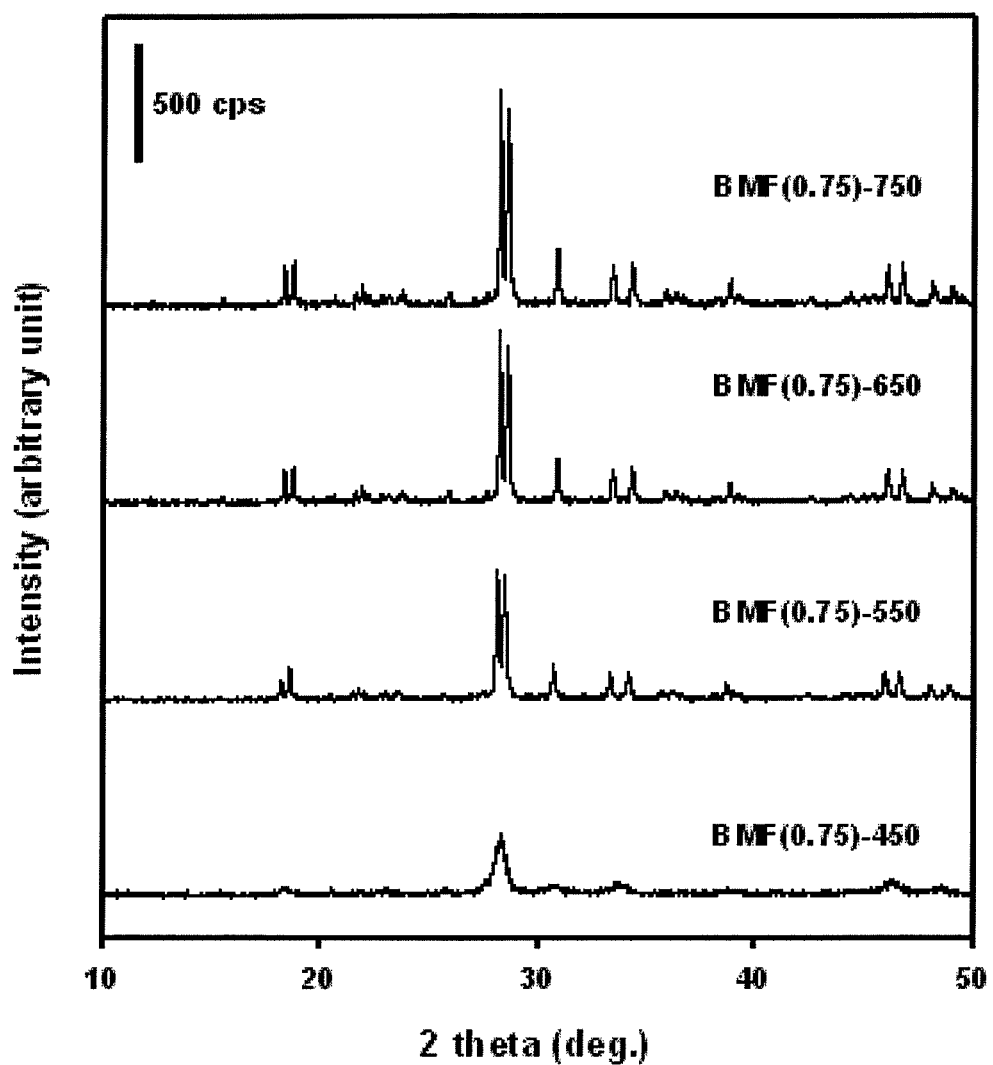
FIG. 3 shows X-ray diffraction pattern of complex oxide catalyst of Bi/Mo/Fe (molar ratio=1.0:1.0:0.75) catalyst prepared in comparative Example 1 at various calcination temperature.

The diffraction pattern of the BMF catalyst was analyzed, and provided in FIG. 3. According to X-ray diffraction analysis, thus prepared catalyst shows no change in phase depending on the calcination temperature. X-ray diffraction pattern of a catalyst sintered at 450° C. shows that crystallinity decreases and amorphous portion increases (FIG. 3).

Example 3

Preparation of BMF Catalyst Comprising Bi and Mo in a Molar Ratio of 3:2

Complex metal oxide catalysts that are different from those prepared in Example 1 in the amount of ingredients were prepared. To prepare a catalyst comprising Bi, Mo and Fe in a molar ratio of 3:2:1, 5.8 g of bismuth nitrate and 3.0 g of nitric acid were added in 21 g of distilled water, and sufficiently stirred at 60° C. 1.6 g of iron nitrate and 1.0 g of nitric acid were also added in 7.0 g of distilled water, and sufficiently stirred at 60° C. These two solutions were slowly added while stirring in the mixture of 1.4 g of ammonium molybdate and 14 g of distilled water. The pH value of the solution was adjusted to 5.0 by slowly adding ammonia water ($NH_4OH$, Daekwang Chemistry, 28%).

Co-precipitated solid products were obtained with an evaporator while hydrothermal reaction was conducted at 60° C., and dried with a drier at 110° C. for 24 hours. Subsequently, the solid product was calcined in an electric furnace at 550° C. to prepare 3.9 g of complex oxide catalyst. The catalyst was denoted as 'BMF'. The yield of the synthesized BMF' catalyst was 94% based on bismuth, molybdenum, and iron oxide (Table 2).

Surface area, pore volume and X-ray diffraction pattern of thus obtained BMF catalyst were analyzed, and the results are provided in Table 2.

TABLE 2

Physicochemical properties of BMF' catalyst

| Catalyst | X-ray diffraction analysis | Surface area ($m^2/g$) | Pore volume ($cm^3/g$) |
|---|---|---|---|
| BMF' | $Bi_3Mo_2FeO_{12}$ | 4.8 | 0.03 |

As shown in Table 2, only the diffraction peaks of $Bi_3Mo_2FeO_{12}$ were observed as a result of X-ray diffraction pattern of BMF'.

Comparative Example

Preparation of BMF Catalyst Comprising Bi and Mo in a Molar Ratio of 1:1 at Various Calcination Temperature To compare the activity of complex oxide catalysts, catalysts with various molar ratios of Bi and Mo were prepared as described in Example but without using Fe. 16.5 g of bismuth nitrate and 8.5 g of nitric acid were added in 60 g of distilled water, and sufficiently stirred at 60° C. This solution was slowly added in the mixture of 6.0 g of ammonium molybdate and 60 g of distilled water while stirring. The pH value of the solution was adjusted to 5.0 by slowly adding ammonia water. Co-precipitated solid products were obtained by using evaporator while a hydrothermal reaction was conducted at 60° C., and dried at 110° C. for 24 hours.

The products were sintered in an electric furnace at 550° C. to provide a comparative BM catalyst. Details of thus obtained catalyst are shown in Table 3. The metal oxide catalyst was denoted as BM with the molar amount of Mo relative to Bi. BM 1.0 refers to a metal oxide catalyst comprising Bi and Mo in a molar ratio of 1:1.

Yield, surface area and X-ray diffraction pattern of the BMF catalyst were analyzed, and the results are provided in Table 3.

TABLE 3

Physicochemical properties of BM catalyst

| Catalyst | Yield (%) | X-ray diffraction analysis | Surface area ($m^2/g$) |
|---|---|---|---|
| BM0.12 | 93 | $Bi_2O_3 \cdot 3MoO_3$ ($\alpha$-phase) | 4.0 |
| BM0.23 | 94 | $Bi_2O_3 \cdot 3MoO_3 > MoO_3$ | — |
| BM1.00 | 95 | $Bi_2O_3 \cdot 2MoO_3$ ($\beta$-phase) | 18.8 |
| BM1.53 | 96 | $Bi_2O_3 \cdot 3MoO_3 > Bi_2O_3 \cdot 2MoO_3$, $Bi_2O_3 \cdot MoO_3$ | — |
| BM2.01 | 96 | $Bi_2O_3 \cdot MoO_3$ ($\gamma$-phase) | 6.2 |
| BM2.27 | 99 | $Bi_2O_3 \cdot MoO_3 > Bi_4MoO_9$ | — |
| BM2.66 | 97 | $Bi_2O_3 \cdot MoO_3 > Bi_4MoO_9$ | — |

As shown in Table 3, $\alpha$-phase Bi Mo oxides mainly exist at a relatively higher Mo content, while only) $\beta$- and $\gamma$-phase diffraction peaks were observed when Bi content is higher.

Test Example 1

Oxidative Dehydrogenation of 1-Butene

Oxidative dehydrogenation of 1-butene was conducted in an atmospheric pressure reactor in the presence of catalysts prepared in Examples 1-3 and Comparative Example.

The catalyst (0.5 g) was filled in a stainless pipe (outer diameter of 0.62 inch and inner diameter of 0.44 inch) at WHSV of 2.4 $h^{-1}$ relative to 1-butene, and activated at 550° C. for 2 hours under the flow of nitrogen and oxygen. Butane, air and water (molar ratio=1.0:3.75:5.0) were mixed at 420° C. by using a mass flow controller, and the mixture was supplied into a reactor. Water was supplied with a high feed accuracy and evaporated in an evaporator before being mixed.

The products of the ODH of 1-butene were analyzed using a gas chromatography (Varian CP3800) equipped with a thermal conductivity detector (TCD) and a flame ionization detector (FID). $CO_2$ and $C_1$-$C_4$ hydrocarbon were analyzed by using a PORAPAK Q packed column (⅛"×2 m, maintained at 60° C.) and a CP—$Al_2O_3$ column, respectively. During oxidative dehydrogenation, double bond migration isomerization between 1-butene and 2-butene, skeletal isomerization and hydrogenation are much faster than dehydrogenation, decomposition and combustion, and 2-butene, iso-butene, n-butane and iso-butane can convert into butadiene. Thus, they are considered as reactants. The conversion of 1-butene, the selectivity of 1,3-butadiene and the 1,3-BD yield are defined as follows.

Mathematical formula 1
$$\text{Conversion (\%)} = \frac{\text{Moles of 1-butene reacted (except 2-, \textit{iso}-butene, \textit{n}- and \textit{iso}-butane)}}{\text{Moles of 1-butene fed}} \times 100$$

$$\text{Selectivity (\%)} = \frac{\text{Moles of 1, 3-butadiene formed}}{\text{Moles of 1-butene reacted}} \times 100 \quad \text{Mathematical formula 2}$$

(except 2-, *iso*-butene, *n*- and *iso*-butane)

$$\text{Yield (\%)} = \frac{\text{Moles of 1, 3-butadiene formed}}{\text{Moles of 1-butene fed}} \times 100 \quad \text{Mathematical formula 3}$$

Reactions were conducted by using the aforementioned devices as described above in the presence of BM and BMF 0.75 catalyst prepared in Example 2 and Comparative Example, respectively. The results are provided in Tables 4 and 5.

TABLE 4

Results of ODH of 1-butene in the presence of BM catalyst of comparative example (reaction time: 400 minutes)

| Catalyst | Component (molar ratio) Bi | Mo | Conversion (%) | 1,3-Butadiene Selectivity (%) | 1,3-Butadiene Yield (%) |
|---|---|---|---|---|---|
| BM 0.12 | 0.12 | 1.0 | 16.7 | 92.8 | 15.5 |
| BM 0.23 | 0.23 | 1.0 | 30.7 | 96.7 | 29.7 |
| BM 1.00 | 1.00 | 1.0 | 37.4 | 95.9 | 35.9 |
| BM 1.53 | 1.53 | 1.0 | 30.3 | 96.8 | 29.3 |
| BM 2.00 | 2.00 | 1.0 | 10.9 | 69.7 | 7.6 |
| BM 2.27 | 2.27 | 1.0 | 0.6 | 24.2 | 0.1 |
| BM 2.66 | 2.66 | 1.0 | 0.4 | 34.1 | 0.1 |

TABLE 5

Results of oxidative dehydrogenation of 1-butene in the presence of BMF 0.74 catalyst of example 3 (reaction time: 400 minutes)

| Catalyst | calcination temperature (° C.) | Conversion (%) | 1,3-BD selectivity (%) | 1,3-Butadiene yield (%) |
|---|---|---|---|---|
| BMF 0.75-450 | 450 | 75.5 | 95.9 | 72.4 |
| BMF 0.75-550 | 550 | 68.5 | 96.0 | 65.8 |
| BMF 0.75-650 | 650 | 38.5 | 97.1 | 37.4 |
| BMF 0.75-750 | 750 | 6.7 | 100 | 6.7 |

In BM catalyst, as the Bi content increased, the conversion and the 1,3-BD yield increases at a particular point and then decreased. In particular, BM 1.0 catalyst comprising Bi and Mo in a molar ratio of 1:1 was the highest in conversion (37%) and 1,3-butadiene yield (32%). BM 1.0 catalyst comprises mainly β-phase Bi Mo oxide as shown in comparative example 2. BMF 0.75 catalyst was sintered at various temperature in the range of 450-750° C. to study the effect of the calcination temperature, and the results are provided in Table 5. At the initial stage, BMF 0.75-450 catalyst calcined at a relatively lower temperature showed a higher conversion (75.5%) and 1,3-BD yield (72%), while BMF 0.75-750 catalyst calcined at 750° C. showed a considerably low conversion of 6.7%.

Although BMF 0.75-550 catalyst is lower than BMF 0.75-450 catalyst in conversion and yield, the ODH of 1-butene described below was conducted in the presence of a catalyst sintered at 550° C., considering the inactivation of catalyst caused by the rising temperature during the exothermal ODH.

Test Example 2

ODH of 1-Butene

Reactions were conducted in the presence of BMF and BMF' catalysts prepared in Examples 1 and 3 as described in Test Example 1 by using the aforementioned devices. The results are provided in Table 6.

TABLE 6

Results of ODH of 1-butene in the presence of BMF catalyst (reaction time: 400 minutes)

| Catalyst | Component (molar ratio) | | | Conversion (%) | 1,3-BD yield (%) | Selectivity (%) | | |
|---|---|---|---|---|---|---|---|---|
| | Bi | Mo | Fe | | | Decomposed products | 1,3-butadiene | $CO_x$ |
| BMF 0.1 | 1 | 1 | 0.10 | 37.6 | 36.7 | 0.4 | 97.7 | 1.9 |
| BMF 0.2 | 1 | 1 | 0.20 | 41.8 | 40.5 | 0.3 | 96.9 | 2.8 |
| BMF 0.35 | 1 | 1 | 0.35 | 57.7 | 55.6 | 0.2 | 96.3 | 3.4 |
| BMF 0.5 | 1 | 1 | 0.50 | 64.2 | 62.0 | 0.2 | 96.5 | 3.2 |
| BMF 0.65 | 1 | 1 | 0.65 | 72.9 | 69.1 | 0.4 | 94.8 | 4.8 |
| BMF 0.75 | 1 | 1 | 0.75 | 68.5 | 65.8 | 0.3 | 96.0 | 3.7 |
| BMF 0.85 | 1 | 1 | 0.85 | 60.1 | 57.9 | 0.3 | 96.3 | 3.3 |
| BMF 1.00 | 1 | 1 | 1.00 | 60.5 | 57.6 | 0.4 | 95.2 | 4.5 |
| BMF 1.25 | 1 | 1 | 1.25 | 47.7 | 45.8 | 0.3 | 96.0 | 3.7 |
| BMF' | 3 | 2 | 1.00 | 71.4 | 67.8 | 0.5 | 94.9 | 4.7 |

In BMF catalyst, the Fe content was shown effective in increasing the conversion and the 1,3-BD yield (BMF0.65 catalyst showed the highest conversion (73%) and the 1,3-BD yield (69%)), while an excessive Fe content reduced the conversion and the 1,3-BD yield due to masking of active sites of the catalyst. This is because it appears Fe Mo oxides blocks the active sites at a relatively higher content of Fe although the incorporation of Fe stabilizes the structure and produces new active sites.

BMF' catalyst comprising Bi, Mo and Fe in a molar ratio of 3:2:1 exhibits a similar activity, while showing a relatively high conversion (71%) and the 1,3-BD yield (68%).

Test Example 3

ODH of 1-Butene

To measure the deactivation of catalysts, oxidative dehydrogenation of 1-butene was conducted in the presence of BMF 0.65 catalyst, which was prepared in Example 1 and ascertained in Test Example 2 as the highest in activity. Conversion and selectivity were measured at various reaction times, and the results are provided in Table 7.

TABLE 7

Results of ODH of 1-butene in the presence of BMF catalyst

| Reaction time (hr) | Conversion (%) | 1,3-BD yield (%) | Selectivity (%) | | |
|---|---|---|---|---|---|
| | | | Decomposed products | 1,3-Butadiene | COx |
| 0.2 | 70.4 | 66.3 | 0.4 | 94.2 | 4.9 |
| 6.5 | 72.9 | 69.1 | 0.4 | 94.8 | 4.8 |
| 120 | 72.1 | 68.5 | 0.4 | 95.0 | 4.7 |

BMF 0.65 catalyst showed little catalytic deactivation for 120 hours from the beginning of the reaction, while maintaining 95% or higher of selectivity toward 1,3-butadiene. This ascertains that BMF 0.65 catalyst is very effective in oxidative dehydrogenation of 1-butene.

As described above, a process of preparing a BMF catalyst provided in the present invention is simple and advantageous in reproducibility. A complex metal oxide catalyst herein shows superior activity in 1-butene oxidative dehydrogenation with less deactivation. The use of a catalyst herein enables the preparation of a higher-priced 1,3-butadiene from 1-butene (or $C_4$-raffinate to 1,3-butadiene) with the catalytic activity maintained for a long period of time. A process of preparing 1,3-butadiene can be achieved by the present invention, and this helps us to efficiently meet the demand of 1,3-butadiene despite high oil prices.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:
1. A Bi/Mo/Fe complex metal oxide catalyst for the preparation of 1,3-butadiene, the catalyst comprising Bi, Mo and Fe in a molar ratio of 1:1:0.5-1.25, and comprising $Bi_3FeMo_2O_{12}$ phase and $Fe_2(MoO_4)_3$ phase.

2. The Bi/Mo/Fe catalyst of claim 1,
wherein the catalyst consists essentially of Bi, Mo and Fe in a molar ratio of 1:1:0.5-1.25, and comprising $Bi_3FeMo_2O_{12}$ phase and $Fe_2(MoO_4)_3$ phase.

3. A Bi/Mo/Fe complex metal oxide catalyst comprising:
Bi, Mo, and Fe in a molar ratio of 1:1:0.5-1.25, and comprising $Bi_3FeMo_2O_{12}$ phase and $Fe_2(MoO_4)_3$ phase,
wherein the catalyst is configured for the preparation of 1,3-butadiene.

4. A process of preparing 1,3-butadiene comprising conducting an oxidative dehydrogenation of 1-butene in the presence of the catalyst of claim 1.

* * * * *